(12) United States Patent
Love et al.

(10) Patent No.: US 8,569,046 B2
(45) Date of Patent: Oct. 29, 2013

(54) MICROARRAY WITH MICROCHANNELS

(75) Inventors: John Christopher Love, Somerville, MA (US); Eliseo Papa, Brescia (IT); Craig M. Story, Salem, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 182 days.

(21) Appl. No.: 12/390,279

(22) Filed: Feb. 20, 2009

(65) Prior Publication Data

US 2010/0216228 A1    Aug. 26, 2010

(51) Int. Cl.
*C12M 1/34* (2006.01)
*C12M 3/00* (2006.01)
*C40B 30/06* (2006.01)
*C40B 40/02* (2006.01)

(52) U.S. Cl.
USPC .............. 435/288.4; 506/7; 506/12; 506/13; 506/15; 506/32; 506/33; 216/39; 216/52

(58) Field of Classification Search
USPC .......... 506/7, 12, 13, 15, 32, 33; 216/39, 52
See application file for complete search history.

(56) References Cited

U.S. PATENT DOCUMENTS

| 8,309,035 | B2 | 11/2012 | Chen et al. |
| 8,309,317 | B2 | 11/2012 | Chen et al. |
| 2002/0141906 | A1 | 10/2002 | Caramanica |
| 2004/0096960 | A1 | 5/2004 | Burd Mehta et al. |
| 2006/0087911 | A1 | 4/2006 | Herz et al. |
| 2006/0228725 | A1 | 10/2006 | Salafsky |
| 2007/0264665 | A1 | 11/2007 | Akhavan-Tafti |

FOREIGN PATENT DOCUMENTS

WO    WO-2007035633 A2    3/2007

OTHER PUBLICATIONS

International Search Report for PCT/US10/24733, dated Apr. 8, 2010.

*Primary Examiner* — Nathan Bowers
*Assistant Examiner* — Gautam Prakash
(74) *Attorney, Agent, or Firm* — Brenda Herschbach Jarrell; John J. Cahill; Choate, Hall & Stewart, LLP

(57) ABSTRACT

A microarray formed in a planar surface of a moldable slab, the microarray including a plurality of microwell sets comprising a plurality of microwells formed in the planar surface of the moldable slab, each microwell being sized to contain at least a single cell, and a plurality of microchannels formed in the planar surface of the moldable slab, the plurality of microchannels being configured to permit liquid from a first region of the microarray to transit to a second region of the microarray.

16 Claims, 8 Drawing Sheets

MICROARRAY WITH MICROCHANNELS

BACKGROUND

Isolation of cells is typically an important part of medical research, such as in the screening and retrieving of individual antibody-secreting cells. In certain circumstances, a medical researcher may desire to isolate individual cells from a suspension containing a large number of cells in order to perform further research. One technique includes the use of a microarray that includes microwells. The suspension of cells is placed on the microarray, thereby allowing a small number of cells to settle into individual microwells. In certain circumstances, a substrate is placed on the microarray to assist in the isolation of cells and to allow for the creation of a printed microarray. Excess residual liquid between the microarray and substrate can cause unreliable results.

SUMMARY

In general, in an aspect, the invention provides a microarray formed in a planar surface of a moldable slab, the microarray including a plurality of microwell sets including a plurality of microwells formed in the planar surface of the moldable slab, each microwell being sized to contain at least a single cell, and a plurality of microchannels formed in the planar surface of the moldable slab, the plurality of microchannels being configured to permit liquid from a first region of the microarray to transit to a second region of the microarray.

Implementations of the invention may provide one or more of the following features. The microchannels include first and second sets of microchannels, wherein the first and second sets of microchannels form a lattice and are in fluid communication, wherein the lattice defines a plurality of interlineal regions. The at least one microwell set is disposed in at least one of the interlineal regions. The configuration of the lattice of microchannels is selected from the group consisting of square and hexagonal. The microchannels are configured such that liquid on the planar surface of the moldable slab is excluded from an interfacial region, via the microchannels, when the planar surface of the moldable slab is placed in contact with a planar surface of a substrate such that a seal is formed between the moldable slab and the substrate.

Implementations of the invention may also provide one or more of the following features. Liquid is excluded from the interfacial region in such a manner that each of the microwells retains sufficient liquid to sustain at least one cell contained therein. The microarray further includes a circumferential microchannel in fluid communication with the microchannels and disposed around the microwell sets. A port is formed through the moldable slab, the port being in fluid communication with the microchannels, the configuration of the port and the microchannels being such that aspiration of the microchannels can be performed via the port. Each of the microwell sets includes at least one microwell that is differentiated from other microwells in the microwell set. The at least one differentiated microwell is located at a predetermined location in each of the microwell sets such that an orientation of the microwell sets can be determined by visual inspection.

Implementations of the invention may further provide one or more of the following features. The at least one differentiated microwell indicates information that can be used to determine a location of each of the microwell sets in the microarray. The information is a column and row number. The differentiated microwell is a different shape from the other microwells in the microwell set. The size of each microwell set is substantially the same as a field of view of a camera used to observe the microwell set. Each of the microwells is in fluid communication with the microchannels. Each of the microwells is substantially 50 µm by 50 µm by 50 µm. Each interlineal region includes sixteen microwell sets arranged in four columns and four rows. The microchannels extend to an outer side edge of the moldable slab.

Various aspects of the invention may provide one or more of the following capabilities. A large number of single cells can be isolated using an array. Liquid trapped between a surface of an array and a second substrate can be efficiently expelled. An orientation of a microwell set can be determined by visual inspection. A location of a microwell within the array can be unambiguously determined by visual inspection. An array can be used to create a printed microarray on a substrate. An array can be tailored such that the printed microarray can be optimized for interrogation by a particular instrument. The quality of printed microarrays can be improved over prior techniques. Each microwell can be sealed by a substrate such that a sub-nanoliter culture can be defined. An array can be optimized for manual and/or automated micromanipulation.

These and other capabilities of the invention, along with the invention itself, will be more fully understood after a review of the following figures, detailed description, and claims.

DETAILED DESCRIPTION

Embodiments of the invention provide techniques for providing an array of microwells that are subdivided by a network of interconnected microchannels. A planar surface of the array is configured be placed in contact with a planar surface of a substrate (e.g., glass, plastic, metal, silicon, rubber) to form an arrangement for use in, for example, discovering new monoclonal antibodies. The array can be arranged in a configuration to allow liquid trapped between the surface of the array, and the substrate to be efficiently expelled to the edges of the array when the array is placed in contact with the substrate. The array can be arranged in a square or hexagonal configuration wherein a plurality of microwells are located in the spaces between microchannels. The microchannels can intersect a ring of channels at the edges of the array and can include ports to allow aspiration of excess media from the system. Furthermore, the shape of individual microwells can be varied to code the location of individual sets of microwells within the array. Other embodiments are within the scope of the invention.

Figure 1:
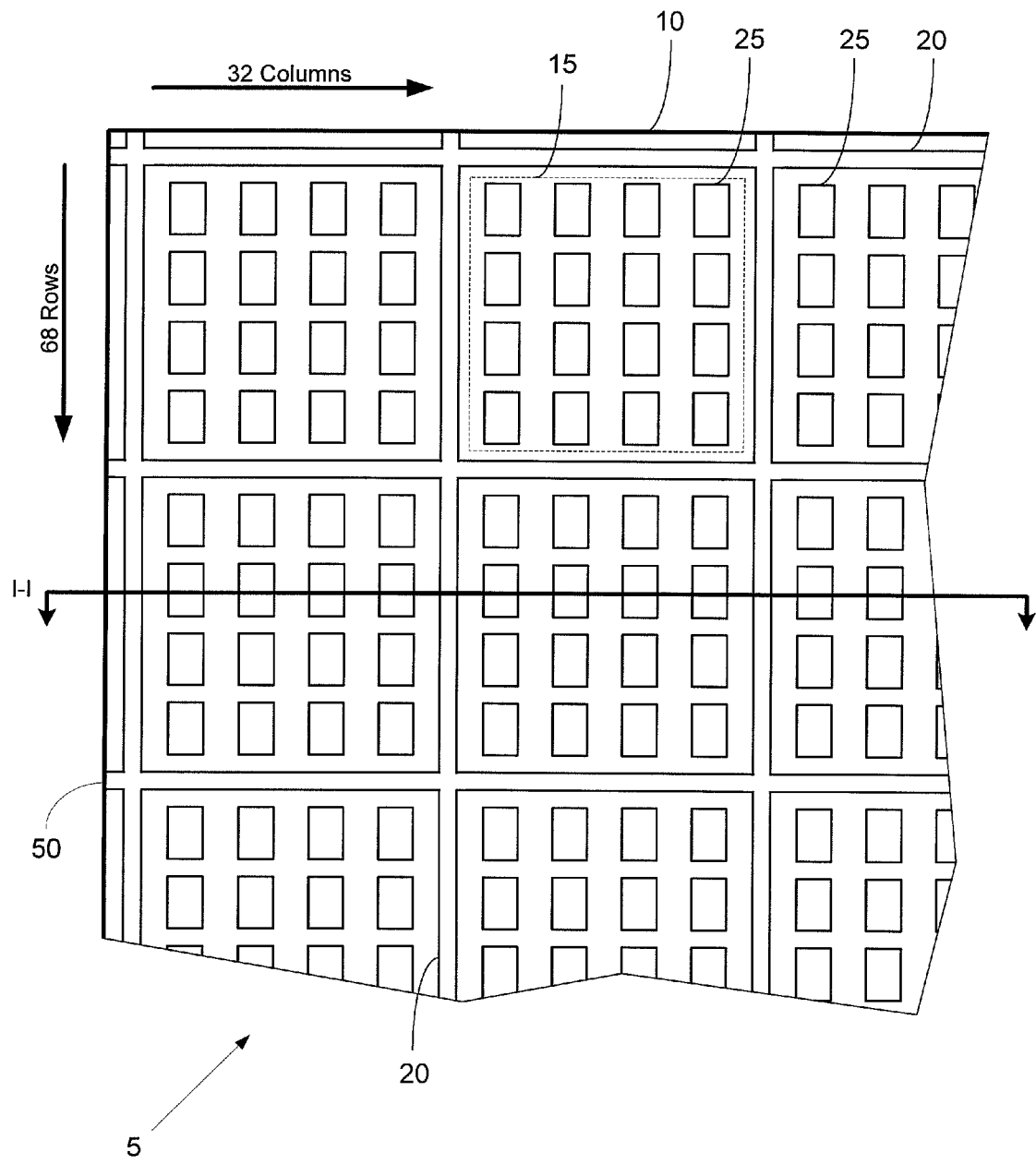
FIG. 1 is a diagram of a portion of an array that includes a plurality of microwell sets and microchannels.
Figure 2:
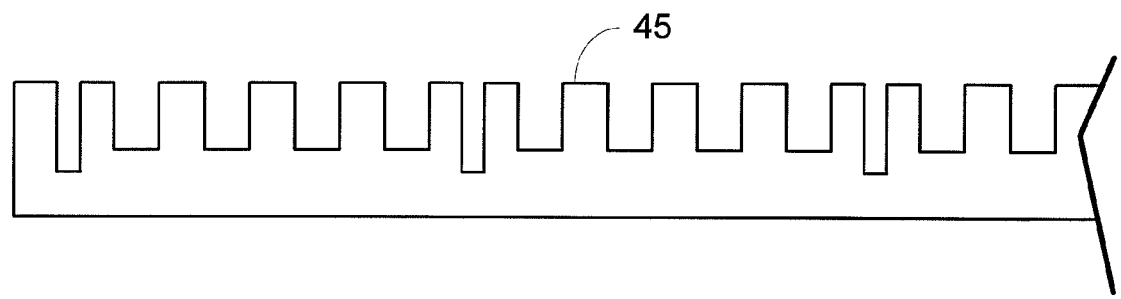
FIG. 2 is a cross-section diagram of the array shown in FIG. 1 taken along line I-I.

Referring to FIGS. 1-2, a portion of an array 5 is shown. Preferably, the array 5 is formed in a conformable composition such as a moldable slab 10. Preferably, the moldable slab 10 is constructed using polydimethylsiloxane (PDMS), although other materials can be used. For example, the moldable slab 10 can also be constructed using variants of silicon, latex, natural rubber, hydrogels (e.g., collagen, polyacrylamide), and/or other gas-permeable, biocompatible materials preferably having a Young's modulus similar to PDMS.

The array 5 preferably includes a plurality of microwell blocks 15 and a plurality of microchannels 20. The microchannels 20 are typically uniformly 10-100 μm wide, and are 1-4 mm apart, although other widths and spacings can also be used. Preferably, the plurality of the microchannels 20 are configured to form a lattice of microchannels that define a plurality of interlineal regions where the microwell blocks 15 can be positioned. For example, the microchannels 20 can be configured in a parallel-perpendicular manner to form a square "city-street" configuration, although other configurations are possible (e.g., the microchannels 20 can be configured in a hexagonal configuration to form a "honeycomb" configuration). The size of the array 5 can vary depending on the application. For example, the dimensions of the array 5 can be configured to be compatible with 25 mm×60 mm coverslips and standard glass slides used for microscopy.

Figure 3:
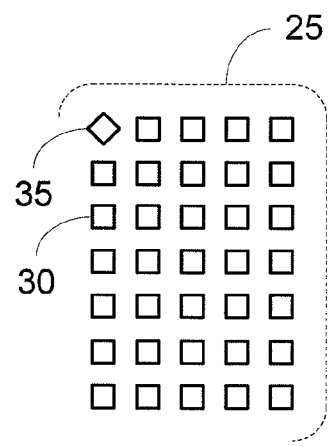
FIG. 3 is a diagram of a microwell set.
Figure 9:
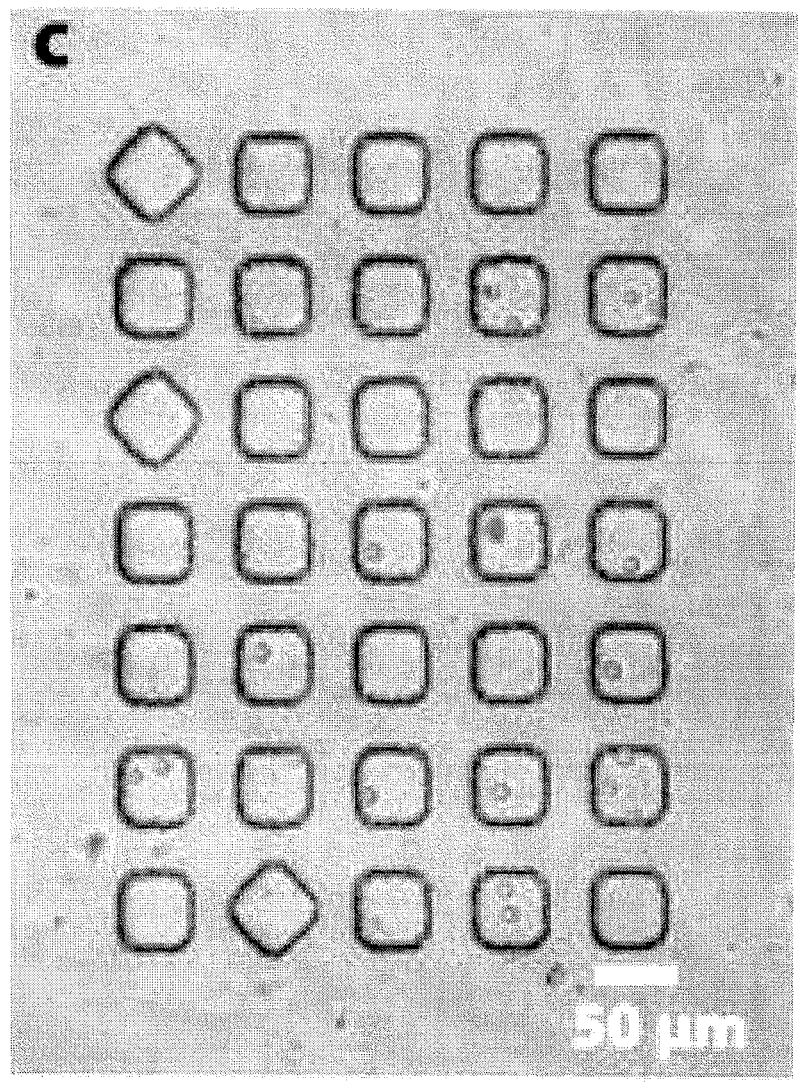
FIG. 9 is a photograph of an exemplary microwell set.

Referring also to FIG. 3, each of the microwell blocks 15 preferably includes a plurality of microwell sets 25 in a four-by-four configuration, which can improve adhesion at the interface of the array 5 and a substrate 40, although other configurations are possible. Preferably, each of the microwell sets 25 are sized such that they are optimized to match the field of view available on a CCD used in typical commercial cameras (e.g., 1360×1024 pixels). The size of the microwell blocks 15 can also be optimized to reduce distortion when the array 5 is combined with the substrate 40. For example, the microchannels 20 can function as a decoupling buffer between the microwell blocks 15 by providing, for example, mechanical stress relief. In tests, the four-by-four configuration of the microwell blocks 15 has been found to reduce distortion in certain circumstances (e.g., a microengraving print from one of the microwell blocks 15 is distorted, while prints from surrounding microwell blocks 15 are satisfactory). Furthermore, while the microwell blocks 15 have been described as including a plurality of microwell sets 25, the array 5 can be configured such that each of the microwell blocks 15 includes a single microwell set. A photograph of an exemplary microwell set that includes isolated cells is shown in FIG. 9. Furthermore, while FIG. 1 shows a 32×64 configuration of the microwell sets 25, other sizes are possible (e.g., the size of a footprint of a 96-well tray).

Each of the microwell sets 25 includes a plurality of cubic microwells 30 arranged in a rectangular 5×7 configuration, having a spacing of 100 μm between microwells. The microwells 30 are preferably cubic and sized to minimize the number of cells loaded per microwell, while facilitating recovery of cells from the microwells by manual micromanipulation (e.g., 50 μm×50 μm×50 μm). For example, the microwells 30 can be sized such an average cell density of 1-3 cells is achieved when a cell-containing suspension is placed on the array 5. The square shape of the microwells can also facilitate assessing the quality of the printed microarray by visual inspection (e.g., the shape can make it easier to distinguish positive elements from artifacts). Notwithstanding the foregoing, the microwells 30 can be configured in other shapes, sizes, and spacings. Furthermore, the microwell sets 25 can be other sizes (e.g., varying number of microwells) and shapes (e.g., rectangular, hexagonal, triangular, etc.).

Each of the microwell sets 25 can be configured such that the orientation of any given microwell set 25 can be determined at a glance. In one technique, one or more predetermined microwells 30 in each of the microwell sets 25 is a different shape and/or configured slightly differently. For example, the top-left microwell (e.g., microwell 35) in each microwell set 25 can be diamond shaped (relative to the rest of the microwells 35, when viewed from above). In this manner, an observer can determine the orientation of the microwell set 25 by observing the location of the diamond-shaped microwell. Other techniques can also be used to connote the orientation of the microwell sets 25 (e.g., using other shaped microwells)

The array 5 is preferably constructed using soft lithographic microengraving techniques. For example, the array 5 can be produced by casting and/or molding (e.g., injection molding, transfer molding, compression molding, etc.) a biocompatible, elastomeric rubber (e.g., PDMS) against a master mold that includes a topographically-patterned surface. The pattern on the master can be transferred to the molded rubber in bas relief. Preferably, the master is a silicon wafer supporting a pattern of photoresist, that is made using standard equipment for photolithography typically found in cleanroom facilities at most universities and/or nanofabrication centers. Exemplary facilities includes Stanford Microfluidics Foundry, the KNI Microfluidic Foundry, and the Harvard Center for Nanoscale Systems. Other techniques and/or facilities can be used to construct the array 5.

Figure 4:
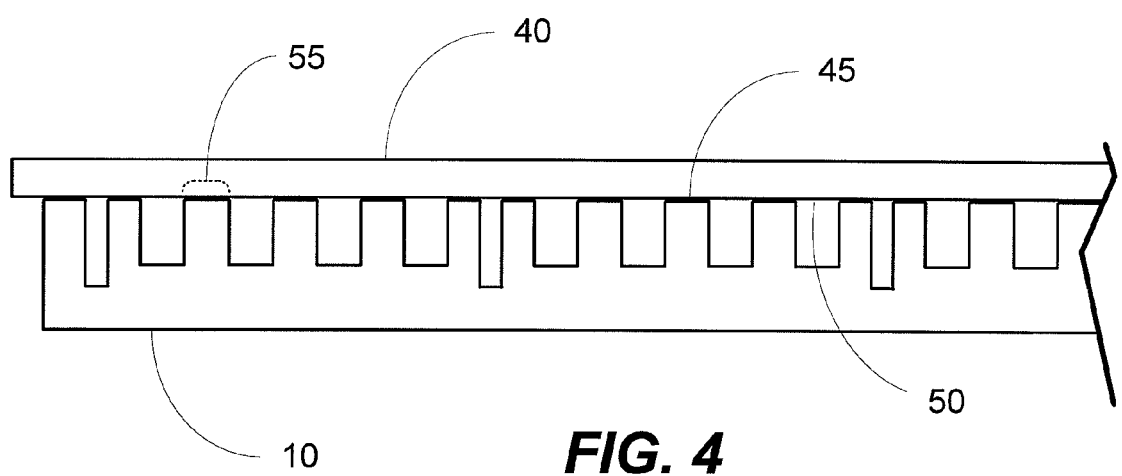
FIG. 4 is a diagram of a portion of a combination of an array and a substrate.

Referring to FIG. 4, the array 5 can be configured for use in microengraving where the array 5 of the microwells 30 is loaded with cells by placing a cell-containing suspension on the array 5 and allowing cells from the suspension to settle into individual microwells 30. The array 5 can be configured to be placed in contact with the substrate 40 (e.g., a glass slide) that has been appropriately functionalized to bind antibodies secreted from the cells. During a period of incubation (e.g., 10-60 minutes), the antibodies secreted from each cell are preferably captured on the surface of the substrate 40, typically resulting in a protein microarray on the substrate 40 where each spot on the array corresponds to a microwell 30 in the array 5.

The array 5 is configured such that it forms a conformal seal with the substrate 40 when the planar surfaces of each are placed in contact (e.g., surfaces 45 and 50, respectively). For example, the configuration of the array 5 can be such that as the array 5 is placed in contact with the substrate 40, liquid trapped between the surface of the array 5 and the surface of the substrate 40 can be efficiently expelled to the edges of the array 5. Thus, the configuration of the array 5 allows fluid to be excluded from the interfacial region (e.g., region 55) and allows the two surfaces to seal. Furthermore, using the disclosed configuration of the array 5, each of the microwells preferably contains sufficient liquid, after a seal has been achieved between the array 5 and the substrate 40, so as to not damage and/or kill any cells contained therein (e.g., each microwell can be sealed to define a sub-nanoliter culture). Excess liquid can be aspirated in multiple locations, such as where each of the microchannels 20 exit the array 5 (e.g., a region 50). Furthermore, the array 5 can be configured for use with clamps such that the array 5 and the substrate 40 are held together and such that pressure can be applied to assist in sealing the microwells 30.

The configuration of the microchannels 20 can vary and one or more aspiration options are possible. For example, aspiration ports can be provided to collect excess liquid that has been excluded from an interfacial region (e.g., of an array and a substrate) as a conformal seal is achieved, and/or has been achieved between the array and the substrate.

Figure 5:
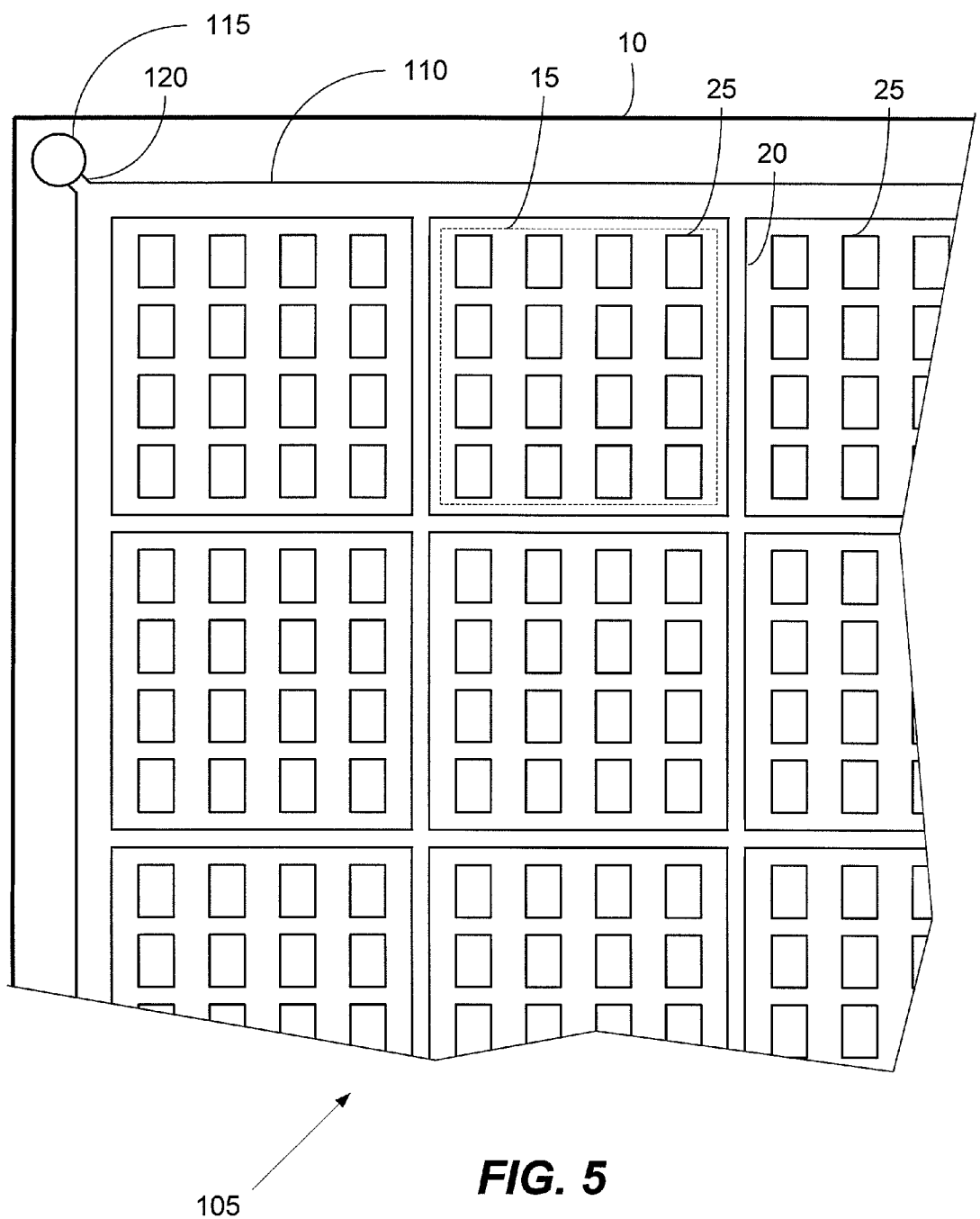
FIG. 5 is a diagram of a portion of an array that includes a port.
Figure 6:
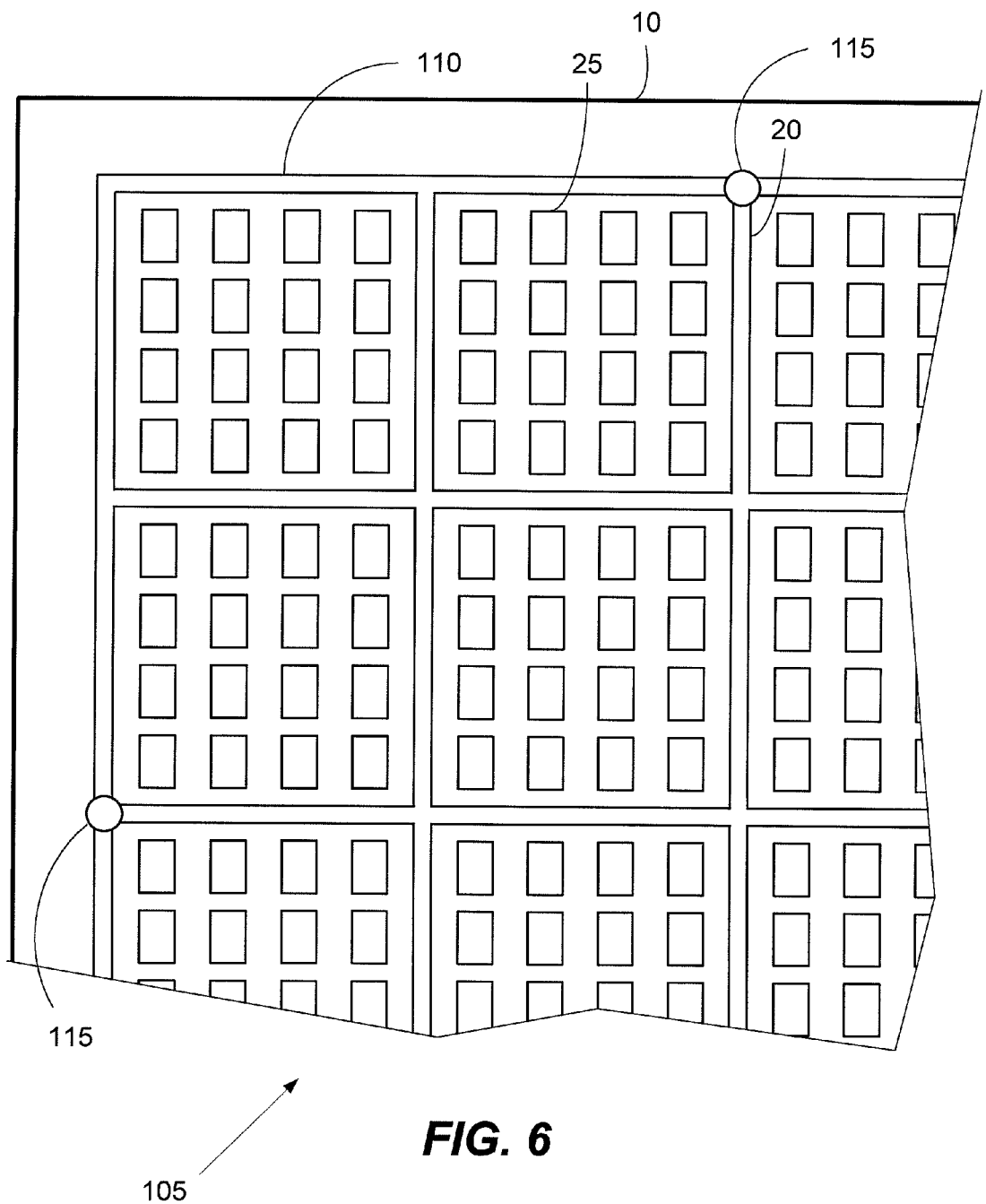
FIG. 6 is a diagram of a portion of an array that includes a plurality of ports.

For example, referring to FIGS. 5 and 6, an array 105 is shown. In the array 105, the configuration of the microchannels 20 is different from that described with respect to the array 5. For example, the microchannels 20 do not extend to the outer edges of the array 105. Rather, the microchannels 20 are in fluid communication with an outer microchannel 110 that forms an outer perimeter around the microwell blocks 15. The outer microchannel 110 can be wider (e.g., 0.5-5 mm wide) than the microchannels 20 (e.g., as shown in FIG. 5) although other widths of the microchannel 110 are possible (e.g., as shown in FIG. 6). Connected to the microchannel 110 can be a port 115. Preferably, the port 115 is a hole that has been formed through the moldable slab 10. Using the port 115, excess liquid can be aspirated from the array 105. Alternatively, the port 115 and/or microchannels 20 can be used as a reservoir to collect excess liquid that has been excluded from the interfacial region, thereby reducing, or even eliminating, the need for aspiration.

The port 115 can be placed in one or more locations on the array 105. For example, referring to FIG. 5, the port 115 can be positioned outside of the outer microchannel 110 and fluidly coupled to the outer microchannel 110 via a coupling microchannel 120. Referring to FIG. 6, multiple ones of the port 115 can also be placed in-line with the outer microchannel 110. Other configurations of the port 115 are also possible (e.g., a port placed in-line with one or more of the microchannels 20).

Figure 7:
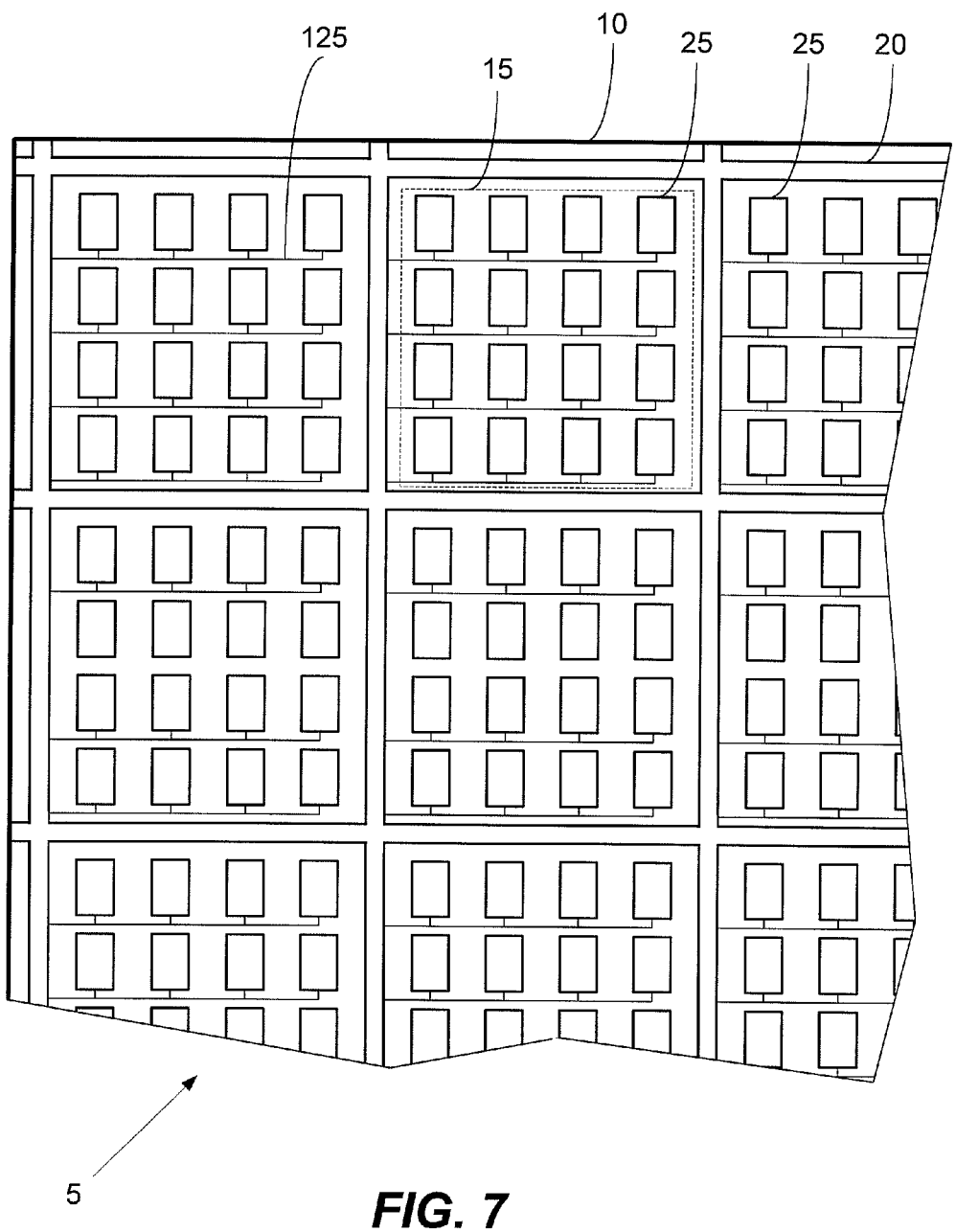
FIG. 7 is a diagram of a potion of an array that includes a plurality of microwell sets and microchannels.

Referring to FIG. 7, the array 5 can also include additional microchannels 125 that can couple each of the microwell sets 25 to the microchannels 20. Using the microchannels 125 it can be possible to wick and/or introduce additional fluids from/to each of the microwell sets 25. For example, small molecules (e.g., drugs, metabolites) may be able to be introduced to a microwell set 25 by diffusion.

Each of the microwell sets 25 can be uniquely coded such that the exact location of any given microwell set 25 on the arrays 5, 105 can be determined. Thus, after locating the position of microwells containing cells of interest by analysis of the array 5, 105, the "address" of each microwell of interest can be identified. In this manner, for example, cells from the microwell of interest can be retrieved at a later time with certainty.

Figure 8:
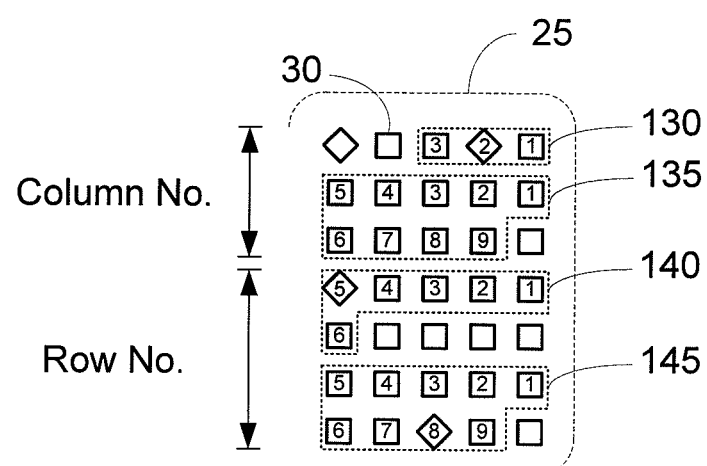
FIG. 8 is a diagram of a microwell set that includes address information.

Referring to FIG. 8, an exemplary coding scheme sections the microwell set 25 into predetermined regions 130, 135, 140, 145, and assigns a predetermined value to individual ones of the microwells 30 within each of the regions. For example, the regions 130, 135 represent the most- and least-significant digits, respectively, of the column in which the microwell set 25 is positioned. Likewise, the regions 140, 145 represent the most- and least-significant digits, respectively, of the row in which the microwell set 25 is positioned. Each of the microwells in each of the regions can be assigned a value (e.g., as shown in FIG. 8). Thus, a number represented in each of the regions 130, 135, 140, and 145 can be identified by changing the shape of the designated microwell (e.g., by using a diamond-shaped microwell to identify the appropriate digit). The number zero can be represented by designating a specific microwell as zero, or, alternatively, the absence of a diamond-shaped microwell in a particular region can indicate the number zero. Thus, interpreting the microwells 35 shown in FIG. 8, an address of column 20, row 58 is shown. Using this coding scheme, a specific microwell on the arrays 5, 105 can be identified with a six-digit number, where the first two digits represent the column of a microwell set of interest, the third and fourth digits represent the row of the microwell of interest, and the last two digits represent the row and column of the microwell within the microwell set of interest. For example, an address of 224757 would represent the bottom right microwell of a microwell set located at column 22, row 47 of the arrays 5, 105.

Other embodiments are within the scope and spirit of the invention. It will be recognized by a person of ordinary skill in the art that various components of the examples described herein can be interchanged and/or substituted with various components in other examples, and that other modifications may be possible. To the extent that any of the material incorporated by reference herein conflicts with the terms of the present disclosure, the present disclosure is intended to be controlling.

Further, while the description above refers to the invention, the description may include more than one invention.

What is claimed is:

1. A microarray formed in a planar surface of a moldable slab, the microarray comprising:
a plurality of microchannels formed in the planar surface of the moldable slab, the plurality of microchannels being configured to form a lattice that defines a plurality of interlineal regions; and
a plurality of microwell sets, each of which is positioned in one of the interlineal regions, wherein each set comprises a plurality of microwells formed in the planar surface of the moldable slab, and each microwell is sized to contain at least a single cell, wherein the microchannels and microwells are arranged and constructed in the planar surface of the moldable slab such that, when the planar surface of the moldable slab is placed in contact with a planar surface of a substrate such that a seal is formed between the moldable slab and the substrate, liquid on the planar surface of the moldable slab is excluded from an interfacial region, via the microchannels.

2. The microarray of claim 1, wherein the microchannels and microwells are arranged and constructed in the planar surface of the moldable slab such that, when the liquid is excluded from the interfacial region via the microchannels, each microwell retains sufficient liquid to sustain at least one cell therein.

3. The microarray of claim 1, wherein the plurality of microchannels comprises a circumferential microchannel in fluid communication with a port such that aspiration of the microchannel can be performed via the port.

4. The microarray of claim 2, wherein the plurality of microchannels comprises a circumferential microchannel in fluid communication with a port such that aspiration of the microchannel can be performed via the port.

5. The microarray of claim 1, wherein the lattice of microchannels has a configuration selected from the group consisting of square and hexagonal.

6. The microarray of claim 1, wherein each of the microwell sets includes at least one microwell that is differentiated from other microwells in the microwell set.

7. The microarray of claim 6, wherein the at least one differentiated microwell is located at a predetermined location in each of the microwell sets such that an orientation of the microwell sets can be determined by visual inspection.

8. The microarray of claim 6, wherein the at least one differentiated microwell indicates information that can be used to determine a location of each of the microwell sets in the microarray.

9. The microarray of claim 8, wherein the information is a column and row number.

10. The microarray of claim 6, wherein the at least one differentiated microwell is a different shape from the other microwells in the microwell set.

11. The microarray of claim 1, wherein each of the microwells is substantially 50 μm by 50 μm by 50 μm.

12. The microarray of claim 1, dimensioned and configured to be compatible with 25 mm×60 mm coverslips and standard glass slides used for microscopy.

13. The microarray of claim 1, wherein each of the microwell sets is sized to match the field of view available to a CCD used in a camera.

14. The microarray of claim 13, wherein the CCD is 1360× 1024 pixels.

15. The microarray of claim 1, wherein each microwell is sized to minimize the number of cells per microwell.

16. The microarray of claim 1, wherein the microchannels and microwells are arranged and constructed such that, when a cell-containing suspension is loaded onto the microarray, cells from the suspension settle into microwells in the microarray, and, when the planar surface of the moldable slab is placed in contact with a planar surface of a substrate such that a seal is formed between the moldable slab and the substrate, liquid on the planar surface of the moldable slab is excluded from an interfacial region, via the microchannels, and sufficient liquid is retained in each of the microwells after the seal has been achieved that cells contained within the microwells are not damaged or killed.

* * * * *